US007144582B1

(12) United States Patent
Ferrari et al.

(10) Patent No.: US 7,144,582 B1
(45) Date of Patent: *Dec. 5, 2006

(54) COMPOSITIONS STRUCTURED WITH AT LEAST ONE POLYMER AND METHODS OF USING THE SAME

(75) Inventors: Véronique Ferrari, Maisons-Alfort (FR); Pascal Simon, Vitry sur Seine (FR)

(73) Assignee: L'Oréal S.A., Paris (FR)

( * ) Notice: Subject to any disclaimer, the term of this patent is extended or adjusted under 35 U.S.C. 154(b) by 61 days.

This patent is subject to a terminal disclaimer.

(21) Appl. No.: 09/685,577

(22) Filed: Oct. 11, 2000

Related U.S. Application Data

(63) Continuation-in-part of application No. 09/618,066, filed on Jul. 17, 2000, now Pat. No. 6,960,339.

(30) Foreign Application Priority Data

Jul. 15, 1999 (FR) ................................ 99 09177

(51) Int. Cl.
*A61Q 1/02* (2006.01)
*A61Q 1/04* (2006.01)
*A61Q 1/06* (2006.01)

(52) U.S. Cl. .................. 424/401; 424/63; 424/64; 424/78.02; 424/78.03

(58) Field of Classification Search ............ 424/70.1, 424/70.11, 70.17, 70.7, 70.9, 63, 64, 65, 59, 424/69, 78.63, 401, 78.03, 78.02; 514/844, 514/845
See application file for complete search history.

(56) References Cited

U.S. PATENT DOCUMENTS

| 2,379,413 A | 7/1945 | Bradley |
| 2,450,940 A | 10/1948 | Cowan et al. |
| 2,463,264 A | 3/1949 | Graenacher |
| 2,662,068 A | 12/1953 | Floyd |
| 2,663,649 A | 12/1953 | Winkler |
| 2,890,097 A | 6/1959 | Coe |
| 2,962,461 A | 11/1960 | Toussaint et al. |
| 3,086,914 A | 4/1963 | Soloway ............... 167/85 |
| 3,141,787 A | 7/1964 | Goetze et al. |
| 3,148,125 A | 9/1964 | Strianse et al. ............... 167/85 |
| 3,156,572 A | 11/1964 | Carlick et al. |
| 3,157,681 A | 11/1964 | Fischer |
| 3,255,082 A | 6/1966 | Barton |
| 3,341,465 A | 9/1967 | Kaufman et al. |
| 3,412,115 A | 11/1968 | Floyd et al. |
| 3,615,289 A | 10/1971 | Felton |
| 3,645,705 A | 2/1972 | Miller et al. ............... 44/7.5 |
| 3,778,394 A | 12/1973 | Lovald et al. |
| 3,819,342 A | 6/1974 | Gunderman et al. |
| 3,857,960 A | 12/1974 | Mackles |
| 3,926,655 A | 12/1975 | Miles |
| 3,937,811 A | 2/1976 | Papantoniou et al. |
| 3,969,087 A | 7/1976 | Saito et al. |
| 4,049,792 A | 9/1977 | Elsnau |
| 4,051,159 A | 9/1977 | Tsoucalas et al. |
| 4,062,819 A | 12/1977 | Mains et al. |
| RE29,871 E | 12/1978 | Papantoniou et al. |
| 4,128,436 A | 12/1978 | O'Hara et al. |
| 4,137,306 A | 1/1979 | Rubino et al. |
| 4,148,875 A | 4/1979 | Barnett et al. |
| 4,150,002 A | 4/1979 | Drawert et al. |
| 4,247,411 A | 1/1981 | Vanlerberghe et al. |
| 4,275,054 A | 6/1981 | Sebag et al. |
| 4,275,055 A | 6/1981 | Nachtigal et al. ............ 424/70 |
| 4,278,658 A | 7/1981 | Hooper et al. |
| 4,279,658 A | 7/1981 | Harvey et al. |
| 4,337,298 A | 6/1982 | Karim et al. |
| 4,341,671 A | 7/1982 | Bolze et al. |
| 4,367,390 A | 1/1983 | Balleys et al. |
| 4,376,194 A | 3/1983 | Tanaka et al. |
| 4,387,090 A | 6/1983 | Bolich, Jr. ................ 424/70 |
| 4,438,240 A | 3/1984 | Tanaka et al. |
| 4,466,936 A | 8/1984 | Schapel |
| 4,536,405 A | 8/1985 | Nara et al. |
| 4,552,693 A | 11/1985 | Hussain et al. ............ 252/522 |
| 4,571,267 A | 2/1986 | Drawert et al. |
| 4,620,492 A | 11/1986 | Vogg et al. |
| 4,655,836 A | 4/1987 | Drawert et al. |
| 4,663,428 A | 5/1987 | Okitu et al. |
| 4,699,779 A | 10/1987 | Palinczar |
| 4,712,571 A | 12/1987 | Remz et al. |

(Continued)

FOREIGN PATENT DOCUMENTS

CA          1319306          6/1988

(Continued)

OTHER PUBLICATIONS

English language DERWENT abstract of JP A 62061911, (Mar. 1987).

(Continued)

*Primary Examiner*—Jyothsna Venkat
(74) *Attorney, Agent, or Firm*—Finnegan, Henderson, Farabow, Garrett & Dunner, L.L.P.

(57) ABSTRACT

A structured cosmetic composition and process of structuring a cosmetic composition comprising at least one amphiphilic compound, at least one dyestuff, and at least one continuous liquid fatty phase structured with a sufficient amount of at least one structuring polymer, wherein the structured composition is in the form of a non-migrating and wax-free solid and wherein the at least continuous liquid fatty phase, the at least one structuring polymer, the at least one amphiphilic compound, and the at least one dyestuff form a physiologically acceptable medium.

10 Claims, No Drawings

U.S. PATENT DOCUMENTS

| | | |
|---|---|---|
| 4,724,137 A | 2/1988 | Hoppe et al. |
| 4,769,285 A | 9/1988 | Rasmussen |
| 4,806,338 A | 2/1989 | Smith .................. 424/47 |
| 4,806,345 A | 2/1989 | Bhattacharyya .............. 424/70 |
| 4,820,765 A | 4/1989 | Whyzmuzis |
| 4,822,601 A | 4/1989 | Goode et al. |
| 4,871,536 A | 10/1989 | Arraudeau et al. .......... 424/59 |
| 4,937,069 A | 6/1990 | Shin |
| 4,952,245 A * | 8/1990 | Iwano et al. |
| 5,034,219 A | 7/1991 | Deshpande et al. |
| 5,061,289 A | 10/1991 | Clausen et al. |
| 5,069,897 A | 12/1991 | Orr ............................ 424/66 |
| 5,073,364 A | 12/1991 | Giezendanner et al. |
| 5,085,859 A | 2/1992 | Halloran et al. |
| 5,102,656 A | 4/1992 | Kasat |
| 5,166,355 A | 11/1992 | Leistner et al. |
| 5,186,318 A | 2/1993 | Oestreich et al. .............. 206/37 |
| 5,196,260 A | 3/1993 | Dirshl et al. |
| 5,223,559 A | 6/1993 | Arraudeau et al. |
| 5,237,071 A | 8/1993 | Leistner et al. |
| 5,252,323 A | 10/1993 | Richard et al. |
| 5,268,029 A | 12/1993 | Demangeon et al. |
| 5,272,241 A | 12/1993 | Lucarelli et al. .............. 528/15 |
| 5,290,555 A | 3/1994 | Guthauser et al. |
| 5,302,398 A | 4/1994 | Egidio et al. |
| 5,342,894 A | 8/1994 | Robeson et al. |
| 5,362,482 A | 11/1994 | Yoneyama et al. |
| 5,372,852 A | 12/1994 | Titterington et al. |
| 5,389,363 A | 2/1995 | Snyder et al. |
| 5,472,686 A | 12/1995 | Tsubaki et al. |
| 5,486,431 A | 1/1996 | Tuttle et al. |
| 5,489,431 A | 2/1996 | Ascione et al. |
| 5,500,209 A | 3/1996 | Mendolia et al. .............. 424/66 |
| 5,505,937 A | 4/1996 | Castrogiovanni et al. |
| 5,510,452 A | 4/1996 | Santhanam ................ 528/291 |
| 5,536,871 A | 7/1996 | Santhanam ................ 560/196 |
| 5,538,718 A | 7/1996 | Aul et al. |
| 5,538,793 A | 7/1996 | Inokuchi et al. |
| 5,540,853 A | 7/1996 | Trinh et al. ................. 510/101 |
| 5,585,091 A | 12/1996 | Pelzer et al. |
| 5,603,925 A | 2/1997 | Ross et al. .................... 424/65 |
| 5,605,651 A | 2/1997 | Balzer |
| 5,610,199 A | 3/1997 | Cohen et al. |
| 5,612,043 A | 3/1997 | Deprez et al. |
| 5,616,331 A | 4/1997 | Allard et al. |
| 5,618,523 A | 4/1997 | Zysman et al. ............. 424/70.1 |
| 5,620,693 A | 4/1997 | Piot et al. |
| 5,628,029 A | 5/1997 | Demangeon et al. |
| 5,645,632 A | 7/1997 | Pavlin |
| 5,667,770 A | 9/1997 | Szweda et al. ............... 424/64 |
| 5,679,357 A | 10/1997 | Dubief et al. ............... 424/401 |
| 5,683,817 A | 11/1997 | Kenmochi |
| 5,695,747 A | 12/1997 | Forestier et al. |
| 5,702,519 A | 12/1997 | Nitta et al. |
| 5,719,255 A | 2/1998 | Heucher et al. |
| 5,747,625 A | 5/1998 | Furukawa et al. |
| 5,750,125 A | 5/1998 | Lahanas et al. |
| 5,750,127 A | 5/1998 | Rokitowski |
| 5,750,489 A | 5/1998 | Garcia et al. |
| 5,769,902 A | 6/1998 | Samain |
| 5,780,517 A | 7/1998 | Cohen et al. |
| 5,783,657 A * | 7/1998 | Pavlin et al. |
| 5,795,565 A | 8/1998 | Eteve et al. |
| 5,800,816 A | 9/1998 | Brieva et al. ................ 424/63 |
| 5,807,968 A | 9/1998 | Heinrich et al. |
| 5,830,444 A | 11/1998 | Miguel |
| 5,830,483 A | 11/1998 | Seidel et al. |
| 5,837,223 A | 11/1998 | Barone et al. |
| 5,849,275 A | 12/1998 | Calello et al. |
| 5,849,278 A | 12/1998 | Piot et al. |
| 5,849,333 A | 12/1998 | Nordhauser et al. |
| 5,849,909 A | 12/1998 | Richard et al. |
| 5,851,517 A | 12/1998 | Mougin et al. |
| 5,857,903 A | 1/1999 | Ramspeck et al. |
| 5,858,338 A | 1/1999 | Piot et al. |
| 5,866,149 A | 2/1999 | Piot et al. |
| 5,871,764 A | 2/1999 | Diaz et al. |
| 5,874,069 A | 2/1999 | Mendolia et al. .............. 424/65 |
| 5,882,363 A | 3/1999 | Spaulding et al. |
| 5,891,424 A | 4/1999 | Bretzler et al. |
| 5,897,869 A | 4/1999 | Roulier et al. ............... 424/401 |
| 5,902,592 A | 5/1999 | Bara et al. |
| 5,908,631 A | 6/1999 | Arnaud et al. |
| 5,911,974 A | 6/1999 | Brieva et al. .................. 424/64 |
| 5,919,441 A | 7/1999 | Mendolia et al. ......... 424/78.08 |
| 5,925,337 A | 7/1999 | Arraudeau et al. |
| 5,945,095 A | 8/1999 | Mougin et al. |
| 5,945,112 A | 8/1999 | Flynn et al. |
| 5,955,060 A | 9/1999 | Huglin et al. |
| 5,959,009 A | 9/1999 | Konik et al. ................. 524/261 |
| 5,961,998 A | 10/1999 | Arnaud et al. |
| 5,962,452 A | 10/1999 | Haase et al. |
| 5,965,112 A | 10/1999 | Brieva et al. .................. 424/64 |
| 5,972,095 A | 10/1999 | Graves et al. |
| 5,972,354 A | 10/1999 | de la Poterie et al. |
| 5,972,359 A | 10/1999 | Sine et al. |
| 5,976,512 A | 11/1999 | Huber |
| 5,976,514 A | 11/1999 | Guskey et al. |
| 5,981,680 A | 11/1999 | Petroff et al. |
| 5,985,298 A | 11/1999 | Brieva et al. |
| 5,993,787 A | 11/1999 | Sun et al. |
| 5,998,570 A * | 12/1999 | Pavlin et al. |
| 6,001,980 A | 12/1999 | Borzo et al. |
| 6,004,567 A | 12/1999 | Marchi-Lemann et al. |
| 6,007,799 A | 12/1999 | Lee et al. |
| 6,019,962 A | 2/2000 | Rabe et al. |
| 6,036,947 A | 3/2000 | Barone et al. |
| 6,045,782 A | 4/2000 | Krog et al. |
| 6,045,823 A | 4/2000 | Vollhardt et al. |
| 6,051,216 A | 4/2000 | Barr et al. ................. 424/78.35 |
| 6,054,517 A | 4/2000 | Spaulding et al. |
| 6,060,072 A | 5/2000 | Konik et al. ................. 424/401 |
| 6,063,398 A | 5/2000 | Gueret |
| 6,066,328 A * | 5/2000 | Ribier et al. ................. 424/401 |
| 6,074,654 A | 6/2000 | Drechsler et al. ........... 424/401 |
| 6,093,385 A | 7/2000 | Habeck et al. |
| 6,103,249 A | 8/2000 | Roulier et al. ............... 424/401 |
| 6,106,820 A | 8/2000 | Morrissey et al. |
| 6,111,055 A | 8/2000 | Berger et al. |
| 6,132,745 A | 10/2000 | Marchi-Lemann et al. |
| 6,156,325 A | 12/2000 | Farer et al. .................. 424/401 |
| 6,156,804 A | 12/2000 | Chevalier et al. |
| 6,159,455 A | 12/2000 | Habeck et al. |
| 6,165,454 A | 12/2000 | Patel et al. |
| 6,165,971 A | 12/2000 | Oppenlander et al. |
| 6,171,347 B1 | 1/2001 | Kunz |
| 6,177,523 B1 | 1/2001 | Reich et al. ................. 525/459 |
| 6,180,117 B1 | 1/2001 | Berthiaume et al. |
| 6,180,123 B1 | 1/2001 | Mondet |
| 6,190,673 B1 | 2/2001 | Guskey et al. ............... 424/401 |
| 6,197,100 B1 | 3/2001 | Melbouchi |
| 6,203,780 B1 | 3/2001 | Arnaud et al. |
| 6,203,807 B1 | 3/2001 | Lemann |
| 6,214,326 B1 | 4/2001 | Dupuis |
| 6,214,329 B1 | 4/2001 | Brieva et al. |
| 6,221,389 B1 | 4/2001 | Cannell et al. |
| 6,224,851 B1 | 5/2001 | Bara |
| 6,242,509 B1 * | 6/2001 | Berger et al. |
| 6,251,375 B1 | 6/2001 | Bara |
| 6,251,409 B1 | 6/2001 | Hegyi et al. |
| 6,254,876 B1 | 7/2001 | de la Poterie et al. |
| 6,254,877 B1 | 7/2001 | de la Poterie et al. |
| 6,264,933 B1 | 7/2001 | Bodelin et al. |
| 6,268,466 B1 | 7/2001 | MacQueen et al. |

| | | |
|---|---|---|
| 6,280,846 B1 | 8/2001 | Darby et al. |
| 6,287,552 B1 | 9/2001 | Tournilhac et al. |
| 6,325,994 B1 | 12/2001 | Collin et al. |
| 6,348,563 B1 | 2/2002 | Fukada et al. |
| 6,361,764 B1 | 3/2002 | Richard et al. |
| 6,372,235 B1 | 4/2002 | Livoreil et al. |
| 6,376,078 B1 | 4/2002 | Inokuchi |
| 6,383,502 B1 | 5/2002 | Dunshee et al. |
| 6,399,080 B1 | 6/2002 | Bara |
| 6,399,081 B1 | 6/2002 | Nakanishi et al. |
| 6,402,408 B1 * | 6/2002 | Ferrari |
| 6,423,306 B1 | 7/2002 | Caes et al. |
| 6,423,324 B1 | 7/2002 | Murphy et al. |
| 6,428,773 B1 | 8/2002 | Oko et al. |
| 6,432,391 B1 | 8/2002 | Bara |
| 6,447,759 B1 | 9/2002 | Noguchi et al. |
| 6,469,131 B1 | 10/2002 | Lawson et al. |
| 6,475,500 B1 | 11/2002 | Vatter et al. |
| 6,479,686 B1 | 11/2002 | Nakanishi et al. |
| 6,482,400 B1 | 11/2002 | Collin |
| 6,491,931 B1 | 12/2002 | Collin |
| 6,497,861 B1 | 12/2002 | Wang et al. |
| 6,503,522 B1 | 1/2003 | Lawson et al. |
| 6,506,716 B1 | 1/2003 | Delplancke et al. |
| 6,545,174 B1 | 4/2003 | Habeck et al. |
| 6,552,160 B1 | 4/2003 | Pavlin |
| 6,649,173 B1 | 11/2003 | Arnaud et al. |
| 6,682,748 B1 | 1/2004 | De La Poterie et al. |
| 6,716,420 B1 | 4/2004 | Feng et al. |
| 6,726,917 B1 | 4/2004 | Kanji et al. |
| 6,749,173 B1 | 6/2004 | Heiling |
| 6,761,881 B1 | 7/2004 | Bara |
| 6,875,245 B1 | 4/2005 | Pavlin |
| 2001/0014312 A1 | 8/2001 | Nakanishi et al. |
| 2001/0014313 A1 | 8/2001 | Roulier et al. |
| 2001/0028887 A1 | 10/2001 | Douin et al. |
| 2001/0031280 A1 | 10/2001 | Ferrari et al. |
| 2001/0033846 A1 | 10/2001 | Roulier et al. |
| 2002/0010179 A1 | 1/2002 | Richard et al. |
| 2002/0044918 A1 | 4/2002 | Bara |
| 2002/0058053 A1 | 5/2002 | Nakanishi et al. |
| 2002/0081323 A1 | 6/2002 | Nakanishi et al. |
| 2002/0102225 A1 | 8/2002 | Hess et al. |
| 2002/0107314 A1 | 8/2002 | Pinzon et al. |
| 2002/0111330 A1 | 8/2002 | Pinzon et al. |
| 2002/0114771 A1 | 8/2002 | Nakanishi |
| 2002/0114773 A1 | 8/2002 | Kanji et al. |
| 2002/0119171 A1 | 8/2002 | Gruning et al. |
| 2002/0120036 A1 | 8/2002 | Pinzon et al. |
| 2002/0122781 A1 | 9/2002 | Pinzon et al. |
| 2002/0131947 A1 | 9/2002 | Nakanishi |
| 2002/0141958 A1 | 10/2002 | Maio et al. |
| 2002/0150602 A1 | 10/2002 | Livoreil et al. |
| 2002/0159964 A1 | 10/2002 | Nakanishi et al. |
| 2002/0168335 A1 | 11/2002 | Collin |
| 2002/0172696 A1 | 11/2002 | Ferrari |
| 2002/0189030 A1 | 12/2002 | Collin |
| 2002/0192168 A1 | 12/2002 | Blin et al. |
| 2003/0012764 A1 | 1/2003 | Collin |
| 2003/0026772 A1 | 2/2003 | Jager-Lezer et al. |
| 2003/0044367 A1 | 3/2003 | Simon et al. |
| 2003/0086883 A1 | 5/2003 | Feng et al. |
| 2003/0147837 A1 | 8/2003 | Cavazzuti et al. |
| 2003/0161807 A1 | 8/2003 | Lemann |
| 2003/0161848 A1 | 8/2003 | Ferrari et al. |
| 2003/0185780 A1 | 10/2003 | Ferrari et al. |
| 2003/0198613 A1 | 10/2003 | Feng et al. |
| 2004/0013625 A1 | 1/2004 | Kanji |
| 2004/0028636 A1 | 2/2004 | Collin |
| 2004/0042980 A1 | 3/2004 | Kanji et al. |
| 2004/0086478 A1 | 5/2004 | Ferrari |
| 2004/0091510 A1 | 5/2004 | Feng et al. |
| 2004/0126401 A1 | 7/2004 | Collin |
| 2004/0166076 A1 | 8/2004 | Ferrari et al. |
| 2004/0166133 A1 | 8/2004 | Cavazzuti et al. |

FOREIGN PATENT DOCUMENTS

| | | |
|---|---|---|
| CA | 2003346 | 5/1990 |
| DE | 38 39 136 A1 | 5/1990 |
| DE | 38 43 892 A1 | 6/1990 |
| DE | 42 08 297 A1 | 9/1993 |
| DE | 42 34 886 A1 | 4/1994 |
| DE | 195 43 988 A1 | 5/1997 |
| DE | 197 07 309 A1 | 8/1998 |
| DE | 197 50 246 A1 | 5/1999 |
| DE | 199 51 010 A1 | 4/2001 |
| EP | 1 169 997 B1 | 2/1986 |
| EP | 0 295 886 B1 | 12/1988 |
| EP | 0 370 470 B1 | 5/1990 |
| EP | 0 374 332 A1 | 6/1990 |
| EP | 0 412 710 B1 | 2/1991 |
| EP | 0 444 633 A2 | 9/1991 |
| EP | 0 557 196 A1 | 8/1993 |
| EP | 0 602 905 B1 | 6/1994 |
| EP | 0 609 132 B1 | 8/1994 |
| EP | 0 623 670 A2 | 11/1994 |
| EP | 0 628 582 B1 | 12/1994 |
| EP | 0 673 642 B1 | 9/1995 |
| EP | 0 708 114 A1 | 4/1996 |
| EP | 0 749 746 A1 | 12/1996 |
| EP | 0 749 747 A1 | 12/1996 |
| EP | 0 749 748 A1 | 12/1996 |
| EP | 0 775 483 A1 | 5/1997 |
| EP | 0 797 976 A2 | 10/1997 |
| EP | 0 820 764 A1 | 1/1998 |
| EP | 0 847 752 A1 | 6/1998 |
| EP | 0 877 063 B1 | 11/1998 |
| EP | 0 879 592 A2 | 11/1998 |
| EP | 0 887 073 A1 | 12/1998 |
| EP | 0 923 928 A1 | 6/1999 |
| EP | 0 925 780 A1 | 6/1999 |
| EP | 0 928 608 A2 | 7/1999 |
| EP | 0 930 058 B1 | 7/1999 |
| EP | 0 930 060 A1 | 7/1999 |
| EP | 0 943 340 A1 | 9/1999 |
| EP | 0 958 804 A2 | 11/1999 |
| EP | 0 958 805 A2 | 11/1999 |
| EP | 0 958 811 A1 | 11/1999 |
| EP | 0 959 066 A2 | 11/1999 |
| EP | 0 959 091 A1 | 11/1999 |
| EP | 0 976 390 A1 | 2/2000 |
| EP | 0 984 025 A2 | 3/2000 |
| EP | 1 002 514 A1 | 5/2000 |
| EP | 1 031 342 A1 | 8/2000 |
| EP | 1 048 282 A1 | 11/2000 |
| EP | 1 053 742 A1 | 11/2000 |
| EP | 1 062 944 A1 | 12/2000 |
| EP | 1 062 959 A1 | 12/2000 |
| EP | 1 064 919 A1 | 1/2001 |
| EP | 1 064 920 A1 | 1/2001 |
| EP | 1 066 814 A1 | 1/2001 |
| EP | 1 068 854 A1 | 1/2001 |
| EP | 1 068 855 A1 | 1/2001 |
| EP | 1 068 856 A1 | 1/2001 |
| EP | 1 086 945 A1 | 3/2001 |
| EP | 1 090 627 B1 | 4/2001 |
| EP | 1 095 959 A2 | 5/2001 |
| EP | 1 114 636 A1 | 7/2001 |
| EP | 1 213 011 A1 | 6/2002 |
| EP | 1 213 316 A2 | 6/2002 |
| FR | 1 529 329 | 5/1968 |
| FR | 2 232 303 | 3/1975 |
| FR | 2 674 126 | 9/1992 |
| FR | 2 785 179 | 5/2000 |
| FR | 2 796 270 | 1/2001 |

| | | |
|---|---|---|
| FR | 2 796 271 | 1/2001 |
| FR | 2 796 272 | 1/2001 |
| FR | 2 796 273 | 1/2001 |
| FR | 2 796 276 | 1/2001 |
| FR | 2 802 806 | 6/2001 |
| FR | 2 804 017 | 7/2001 |
| FR | 2 804 018 | 7/2001 |
| FR | 2 810 562 | 12/2001 |
| FR | 2 811 225 | 1/2002 |
| FR | 2 811 552 A1 | 1/2002 |
| FR | 2 816 506 | 5/2002 |
| FR | 2 817 739 | 6/2002 |
| FR | 2 817 740 | 6/2002 |
| FR | 2 817 743 | 6/2002 |
| FR | 2 819 399 | 7/2002 |
| FR | 2 819 400 | 7/2002 |
| FR | 2 819 402 | 7/2002 |
| GB | 1 117 129 | 6/1968 |
| GB | 1 194 901 | 6/1970 |
| GB | 1 194 902 | 6/1970 |
| GB | 1 220 069 | 1/1971 |
| GB | 1 273 004 | 5/1972 |
| GB | 1 444 204 | 7/1976 |
| GB | 2 014 852 | 9/1979 |
| GB | 2 014 852 A | 9/1979 |
| GB | 2 021 411 A | 12/1979 |
| GB | 2 147 305 A | 5/1985 |
| GB | 2 196 978 A | 5/1988 |
| JP | 50/58242 | 5/1975 |
| JP | 53043577 A | 4/1978 |
| JP | 56123909 A | 9/1981 |
| JP | 56166276 A | 12/1981 |
| JP | 61065809 A | 4/1986 |
| JP | 62061911 | 3/1987 |
| JP | 2127568 A | 5/1990 |
| JP | 02/200612 | 8/1990 |
| JP | 2216279 A | 8/1990 |
| JP | 3014683 A | 1/1991 |
| JP | 04346909 A | 12/1992 |
| JP | 7179795 A | 7/1995 |
| JP | 7267827 A | 10/1995 |
| JP | 8225316 A | 9/1996 |
| JP | 9/20631 | 1/1997 |
| JP | 09/255560 | 9/1997 |
| JP | 9295922 A | 11/1997 |
| JP | 10/007527 | 1/1998 |
| JP | 10/120903 | 5/1998 |
| JP | 10/212213 | 8/1998 |
| JP | 10259344 A | 9/1998 |
| JP | 11106216 A | 4/1999 |
| JP | 11/335228 | 12/1999 |
| JP | 11/335242 | 12/1999 |
| JP | 11/335254 | 12/1999 |
| JP | 200038321 A | 2/2000 |
| JP | 2000038314 A | 2/2000 |
| JP | 2000038316 A | 2/2000 |
| JP | 2000038317 A | 2/2000 |
| JP | 200086427 A | 3/2000 |
| JP | 2000086429 A | 3/2000 |
| JP | 2000086438 A | 3/2000 |
| WO | WO 86/04916 | 8/1986 |
| WO | 87/03783 | 7/1987 |
| WO | WO 91/12793 | 9/1991 |
| WO | 93/21763 | 11/1993 |
| WO | WO 93/23008 | 11/1993 |
| WO | WO 94/18261 | 8/1994 |
| WO | WO 94/21233 | 9/1994 |
| WO | WO 95/15741 | 6/1995 |
| WO | WO 95/24887 | 9/1995 |
| WO | WO 95/33000 | 12/1995 |
| WO | WO 96/15761 | 5/1996 |
| WO | WO 96/40044 | 12/1996 |
| WO | WO 97/17057 | 5/1997 |
| WO | WO 97/36573 | 10/1997 |
| WO | WO 98/17243 | 4/1998 |
| WO | WO 98/17705 | 4/1998 |
| WO | WO 98/22078 | 5/1998 |
| WO | WO 98/25922 | 6/1998 |
| WO | WO 98/27162 | 6/1998 |
| WO | WO 98/42298 | 10/1998 |
| WO | WO 98/47470 | 10/1998 |
| WO | WO 98/52534 | 11/1998 |
| WO | WO 98/58623 | 12/1998 |
| WO | WO 99/24002 | 5/1999 |
| WO | 00/27350 | 5/2000 |
| WO | WO 00/40216 | 7/2000 |
| WO | 00/61080 | 10/2000 |
| WO | 00/61081 | 10/2000 |
| WO | WO 00/74519 A2 | 12/2000 |
| WO | 01/51020 | 7/2001 |
| WO | 01/52799 | 7/2001 |
| WO | WO 01/97758 A2 | 12/2001 |
| WO | WO 01/97773 A1 | 12/2001 |
| WO | WO 02/03932 A2 | 1/2002 |
| WO | WO 02/03935 A2 | 1/2002 |
| WO | WO 02/03950 A2 | 1/2002 |
| WO | WO 02/03951 A2 | 1/2002 |
| WO | 02/47620 | 6/2002 |
| WO | 02/47658 | 6/2002 |
| WO | 02/49601 | 6/2002 |
| WO | WO 02/47605 A2 | 6/2002 |
| WO | WO 02/47608 A2 | 6/2002 |
| WO | WO 02/47619 A2 | 6/2002 |
| WO | WO 02/47622 A2 | 6/2002 |
| WO | WO 02/47627 A1 | 6/2002 |
| WO | WO 02/47629 A1 | 6/2002 |
| WO | WO 02/47630 A1 | 6/2002 |
| WO | WO 02/49583 A1 | 6/2002 |
| WO | WO 02/055030 A2 | 7/2002 |
| WO | WO 02/055031 A1 | 7/2002 |
| WO | WO 02/056845 A1 | 7/2002 |
| WO | WO 02/056847 A1 | 7/2002 |
| WO | WO 02/056848 A1 | 7/2002 |
| WO | WO 02/092047 A1 | 11/2002 |
| WO | WO 02/092663 A1 | 11/2002 |
| WO | WO 02/102322 A2 | 12/2002 |
| WO | WO 05/013887 A2 | 2/2005 |

OTHER PUBLICATIONS

English language DERWENT abstract of JP 02/200612, (Aug. 1990).
English language DERWENT abstract of JP 09/255560, (Sep. 1997).
English language DERWENT abstract of JP 10/007527, (Jan. 1998).
English language DERWENT abstract of JP 10/212213, (Aug. 1998).
English language DERWENT abstract of EP 0 943 340 A1, (Mar. 1999).
English language DERWENT abstract of EP 1 068 856 A1, (Jul. 2000).
English language DERWENT abstract of FR 2 796 270, (Jul. 1999).
English language DERWENT abstract of FR 2 796 271, (Jul. 1999).
English language DERWENT abstract of FR 2 796 276, (Jul. 1999).
P. Terech, "Low-Molecular Weight Organogelators," in *Specialist Surfactants*, ch. 8, pp. 208-268 (I.D. Robb, ed., 1997).
English language DERWENT abstract of EP 0 820 764 A1.
English language DERWENT abstract of EP 0 923 928 A1.
English language DERWENT abstract of EP 0 925 780 A1.
English language DERWENT abstract of FR 2 811 552 A1.
English language DERWENT abstract of FR 2 816 506.
Milan Jokić et al., *A Novel Type of Small Organic Gelators: Bis(Amino Acid) Oxalyl Amides,* 1995 J. Chem. Soc., Chem. Commun., 1723.

Kenji Hanabusa et al., *Prominent Gelation and Chiral Aggregation of Alkylamides Derived from trans-1,2-Diaminocyclohexane*, Angew. Chem. Int. Ed. Engl. 1996, 35, No. 17, 1949-1951.
Toshimi Shimizu et al., *Stereochemical Effect of Even-Odd Connecting Links on Supramolecular Assemblies Made of 1-Glucosamide Bolaamphiphiles*, J. Am Chem. Soc. 1997, 119, 2812-2818.
Kenji Hanabusa et al., *Terephthaloyl Derivatives as New Gelators; Excellent Gelation Ability and Remarkable Increase of Gel Strength by Adding Polymers*, 1999 Chemistry Letters 767.
Xuzhong Luo et al., *Self-assembled organogels formed by monoalkyl derivatives of oxamide*, 2000 Chem. Commun. 2091-92.
Kenji Hanabusa et al., *Easy Preparation and Gelation of New Gelator Based on L-Lysine*, 2000 Chem. Lett., 1070.
PCT Application No. PCT/IB01/02780; Title: Cosmetic Compositions Containing at Least one Heteropolymer and at Least one Organogelator International Filing Date: Dec. 12, 2001.
Charles M. Hansen, *"The Three Dimensional Solubility Parameter—Key to Paint Component Affinities: I. Solvents, Plasticizers, Polymers, and Resins,"* Journal of Paint Technology, vol. 39, No. 505, Feb. 1967, pp. 104-117.
Yasuda et al., *Novel Low-molecular-weight Organic Gels: N,N', N''-Tristearyltrimesamide/Organic Solvent System*, Chemistry Letters, pp. 575-576, 1996, the month of publication is not available.
Bush Boake Allen, Inc., *Uniclear Formulations*, dated Oct. 13, 1998.
English language DERWENT abstract of DE 42 08 297.
English language DERWENT abstract of DE 195 43 988.
English language DERWENT abstract of DE 199 51 010.
English language DERWENT abstract of DE 38 43 892.
English language DERWENT abstract of DE 42 34 886.
English language DERWENT abstract of EP 0 169 997 B1.
English language DERWENT abstract of EP 0 749 748.
English language DERWENT abstract of FR 2 796 272.
English language DERWENT abstract of FR 2 796 273.
English language DERWENT abstract of FR 2 804 017.
English language DERWENT abstract of FR 2 804 018.
English language DERWENT abstract of FR 2 810 562.
English language DERWENT abstract of FR 2 811 225.
English language DERWENT abstract of FR 2 817 739.
English language DERWENT abstract of FR 2 817 740.
English language DERWENT abstract of FR 2 817 743.
English language DERWENT abstract of FR 2 819 399.
English language DERWENT abstract of FR 2 819 400.
English language DERWENT abstract of JP 9/20631.
English language DERWENT abstract of JP 10/120903.
English language DERWENT abstract of JP 11/335228.
English language DERWENT abstract of JP 11/335242.
English language DERWENT abstract of JP 11/335254.
English language DERWENT abstract of JP 2000038314 A.
English language DERWENT abstract of JP 2000038316 A and JP 2000038317 A.
English language DERWENT abstract of JP 2000038321 A.
English language DERWENT abstract of JP 2000086427 A.
English language DERWENT abstract of JP 2000086429 A.
English language DERWENT abstract of JP 2000086438 A.
Handbook of Cosmetic Science and Tech. Elsevier Advanced Tech., 1st Edition (1994), p. 19.
International Search Report in PCT/FR01/03726, dated Apr. 9, 2002.
Kirk-Othmer, "Encyclopedia of Chemical Technology", Third Edition, vol. 22, John Wiley & Sons, 1983, pp. 332-342.
PCT Application No. PCT/US03/41618; Title: Cosmetic Compositions Comprising a Structuring Agent, Silicone Powder and Swelling Agent Inventor: Shao Xiang Lu, Terry Van Liew, Nathalie Geffroy-Hyland International Filing Date: Dec. 22, 2003.
PCT Application No. PCT/US04/01071; Title: Long Wear Cosmetic Composition Inventor: Balanda ATIS International Filing Date: Jan. 16, 2004.
McCutcheon's vol. 1: Emulsifiers & Detergents North American and International Editions, MC Publishing Co., Glen Rock NJ (1993), pp. 272-273.
Certified English translation of FR 1 529 329.
Estee Lauder MagnaScopic Maximum Volume mascara product packaging, believed to have first been sold in 2003.
Estee Lauder's Response to Plaintiff's First Set of Interrogatories (Nos. 1-6), dated Sep. 27, 2004, in the on-going litigation L'Oreal S.A., et al. v. The Estee Lauder Companies Inc. et al., Civil Action No. 04-1660 (D.N.J.).
French Search Report in FR 0000920 (priority document for PCT/FR01/00229, dated Nov. 10, 2000.
French Search Report in FR 0001004, dated Nov. 10, 2000.
French Search Report in FR 0008084, dated Mar. 28, 2001.
French Search Report in FR 0008913, dated Mar. 20, 2001.
French Search Report in FR 0016161, dated Sep. 6, 2001.
Co-Pending U.S. Appl. No. 10/494,864; Title: Composition Containing an Amino Acid N-Acylated Ester and A Polyamide-Structured UV Filter U.S. Filing Date: Nov. 23, 2004.
English language Derwent abstract of WO 98/25922.
Estee Lauder's Amended Answer and Counterclaims, dated Apr. 21, 2005, in the on-going litigation L'Oreal S.A., et al., v. The Estee Lauder Companies Inc., et al., Civil Action No. 04-1660 (D.N.J.).
Estee Lauder's Response to Plaintiff's Third Set of Interrogatories (Nos. 8-13), dated Jun. 21, 2005, in the on-going litigation L'Oreal S.A., et al. v. The Estee Lauder Companies Inc., et al., Civil Action No. 04-1660 (D.N.J.).
Office Action in co-pending U.S. Appl. No. 09/733,898, dated Apr. 25, 2005.
Office Action in co-pending U.S. Appl. No. 09/733,899, dated May 3, 2005.
Office Action in co-pending U.S. Appl. No. 09/733,900, dated Jun. 2, 2005.
Office Action in co-pending U.S. Appl. No. 09/749,036, dated Apr. 29, 2005.
Office Action in co-pending U.S. Appl. No. 10/012,052, dated Jun. 3, 2005.
Office Action in co-pending U.S. Appl. No. 10/203,254, dated Apr. 22, 2005.
Office Action in co-pending U.S. Appl. No. 10/203,375, dated May 13, 2005.
Office Action in co-pending U.S. Appl. No. 10/312,083, dated Apr. 18, 2005.
Office Action in co-pending U.S. Appl. No. 10/699,780, dated Jun. 15, 2005.
Office Action in co-pending U.S. Appl. No. 10/746, 612, dated Jun. 15, 2005.
Office Action in co-pending U.S. Appl. No. 09/733,896, dated Jul. 13, 2005.
Richard J. Lewis, Sr., "Ricinoleic Acid," Hawley's Condensed Chemical Dictionary 972 (13th. 1997).
International Search Report in PCT/US04/01071, dated Feb. 22, 2005.
International Search Report in PCT/US03/41618, dated Mar. 11, 2005.
Office Action in co-pending U.S. Appl. No. 10/182,830, dated Apr. 4, 2005.
Office Action in co-pending U.S. Appl. No. 10/787,441, dated Apr. 5, 2005.
Office Action in co-pending U.S. Appl. No. 10/312,083, dated Apr. 18, 2005.
Office Action in co-pending U.S. Appl. No. 10/203,254, dated Apr. 22, 2005.
Office Action in co-pending U.S. Appl. No. 09/733,898, dated Apr. 25, 2005.
Office Action in co-pending U.S. Appl. No. 09/749,036, dated Apr. 29, 2005.
Office Action in co-pending U.S. Appl. No. 09/733,899, dated May 3, 2005.
Office Action in co-pending U.S. Appl. No. 10/203,375, dated May 13, 2005.

* cited by examiner

COMPOSITIONS STRUCTURED WITH AT LEAST ONE POLYMER AND METHODS OF USING THE SAME

This application is a Continuation-in-Part application of U.S. patent application Ser. No. 09/618,066, filed Jul. 17, 2000, now U.S. Pat. No. 6,960,339, the disclosure of which is incorporated herein by reference. The present application and U.S. patent application Ser. No. 09/618,066 claim the benefit of priority from French Patent Application Serial No. 9909177, filed Jul. 15, 1999.

The present invention relates to compositions for care of, for treating and for making-up at least one keratinous material, in particular at least one human keratinous material, such as skin, including the scalp, lips, eyelashes and eyebrows, comprising at least one continuous liquid fatty phase gelled with at least one structuring polymer and at least one dyestuff. This invention may be in the form of make-up sticks such as lipsticks and may give a glossy and non-migrating deposit when applied.

Structured continuous liquid fatty phases in cosmetic or dermatological products are known in the art. As used herein, "structured" means gelled and/or rigidified. Structured continuous liquid fatty phases may be found in solid compositions such as deodorants, balms, lip compositions, concealer products and cast foundations. In general, this structuring may be obtained with the aid of waxes or fillers. However, these waxes and fillers have a tendency to make the compositions matte and matte compositions may not be desired. For example, women may desire lip compositions in the form of a tube which deposit glossy films.

As used herein, "continuous liquid fatty phase" means a fatty phase which is liquid at room temperature (25° C.) and at atmospheric pressure (760 mmHg) and which is composed of at least one fatty substance, such as an oil, which is liquid at room temperature. If the continuous liquid fatty phase comprises two or more fatty substances, they should be mutually compatible.

Structured continuous liquid fatty phases may make it possible to control the exudation of the continuous liquid fatty phase from the solid compositions in which they are components. Structuring of the continuous liquid fatty phase may also limit the migration of this phase into wrinkles and fine lines after it has been deposited, for example, on the skin or the lips. A large migration of a continuous liquid fatty phase comprising dyestuffs such as in lip compositions may lead to an unaesthetic effect around the lips which may accentuate the wrinkles and fine lines. Women have cited this migration as a drawback of conventional lip compositions.

The gloss of cosmetic and dermatological compositions may be associated with the nature of the continuous liquid fatty phase. Reduction of the concentration of waxes and fillers in such compositions may increase gloss, but the migration of the continuous liquid fatty phase may increase. In other words, the concentration of waxes and fillers required to prepare cosmetic and dermatological compositions in the form of a stick which have a suitable hardness may limit the gloss of the deposited compositions.

The inventor has found that the observed decrease in gloss of cosmetic and dermatological compositions in the form of a stick which comprise waxes may be associated with the anisotropic crystal structure of the waxes. One aim of the present invention is to provide cosmetic and/or dermatological compositions for the manufacture of wax-free compositions in the form of a stick.

Another subject of the invention is cosmetic and/or dermatological compositions which are useful for the care, make-up and/or treating of at least one keratinous material which may be of suitable hardness to allow preparation of these compositions in the form of a stick, which may be glossy and which may be non-migrating. As used herein, "keratinous material" is meant to comprise hair, lips, skin, scalp and superficial body growths such as eyelashes, eyebrows, and nails.

The inventor has found, surprisingly, that the use of specific polymers may make it possible to structure, even, in some embodiments, in the absence of wax, continuous liquid fatty phases in the form of a stick, which may give a glossy and non-migrating film when applied to a keratinous material.

The invention applies not only to make-up products for at least one keratinous material such as lip compositions, lip pencils, foundations which may be cast in the form of a stick or a dish, concealer products, temporary tattoo products, eyeliners which may be in pencil form, mascara tablets, but also to body hygiene products such as deodorant sticks, and to care products and products for treating at least one keratinous material such as sunscreen and after-sun products which may be in stick form.

In one embodiment, the present invention is directed to a structured composition containing at least one dyestuff and at least one continuous liquid fatty phase, wherein said at least one continuous liquid fatty phase is structured with a sufficient amount of at least one structuring polymer which has a weight-average molecular mass ranging up to 30,000 and which comprises a) a polymeric skeleton comprising repeating units comprising at least one hetero atom, and b) at least one fatty chain, optionally functionalized, comprising from 12 to 120 carbon atoms, chosen from pendant fatty chains and terminal fatty chains which are bonded to the polymeric skeleton, wherein the at least one fatty chain is present in a quantity ranging from 40% to 98% of the total number of all of the repeating units comprising at least one hetero atom and of all the fatty chains, wherein the composition is in the form of a wax-free solid, and wherein the at least one dyestuff, the at least one continuous liquid fatty phase and the at least one structuring polymer form a physiologically acceptable medium. In one embodiment, the at least one structuring polymer has a weight-average molecular mass ranging from 1000 to 10,000.

As used herein, "at least one" means one or more. Also, as used herein, a "wax" is a lipophilic fatty compound which is solid at room temperature (25° C.), undergoes a reversible solid/liquid change of state, has a melting point of greater than 40° C. (which can be up to 200° C.), and has an anisotropic crystal organization in the solid state. The size of the crystals of the wax may be such that the crystals scatter and/or diffuse light, giving the composition a cloudy, relatively opaque appearance. It may be possible to make the wax miscible with oils by bringing the wax to its melting point, and, thereby, to form a microscopically homogeneous mixture but once the mixture has returned to room temperature, recrystallization of the wax occurs. This recrystallization may be responsible for reducing the gloss of the compositions which comprise such wax.

For the purposes of the application, waxes may be chosen from those normally used in cosmetic or dermatological compositions. Non-limiting examples of such waxes include waxes of natural origin, such as beeswax, carnauba wax, candelilla wax, ouricury wax, Japan wax, cork fiber wax, sugar cane wax, paraffin waxes, lignite wax, microcrystalline waxes, lanolin wax, montan wax and ozokerites, hydrogenated oils such as hydrogenated jojoba oil, waxes of synthetic origin, such as polyethylene waxes derived from polymerization of ethylene, waxes obtained by Fischer-Tropsch synthesis, fatty acid esters and glycerides that are solid at 40° C., and silicone waxes such as derivatives of poly(di)methylsiloxane which are solid at 40° C.

The compositions of the present invention may be advantageously self-supporting and may be in a form chosen from a stick or a dish. The compositions may also be in a form chosen from a transparent anhydrous rigid gel and a transparent anhydrous stick wherein the at least one continuous liquid fatty phase may form the continuous phase.

The structure or gelation of the at least one continuous liquid fatty phase may be modified by the nature of the at least one structuring polymer used. The at least one continuous liquid fatty phase of the compositions of the present invention are structured with a sufficient amount of at least one structuring polymer chosen such that a rigid structure such as those in the form of a tube or a stick may be obtained. When these compositions are colored, they may, after they have been applied to a keratinous material, give a glossy deposit of homogeneous color which does not migrate into wrinkles or fine lines of the keratinous material. The compositions which are the subject of the invention comprise at least one structuring polymer which may be soluble in a wide variety of oils.

In one embodiment, the present invention is directed to a structured composition containing at least one dyestuff and at least one continuous liquid fatty phase, wherein said at least one continuous liquid fatty phase is structured with a sufficient amount of at least one structuring polymer which has a weight-average molecular mass ranging up to 30,000 and which comprises a) a polymeric skeleton comprising repeating units comprising at least one non-pendant hetero atom, and b) at least one fatty chain, optionally functionalized, comprising from 12 to 120 carbon atoms, chosen from pendant fatty chains and terminal fatty chains which are bonded to the polymeric skeleton, wherein the at least one fatty chain is present in a quantity ranging from 40% to 98% of the total number of all of the repeating units comprising at least one hetero atom and of all the fatty chains, wherein the composition is in the form of a wax-free solid, and wherein the at least one dyestuff, the at least one continuous liquid fatty phase and the at least one structuring polymer form a physiologically acceptable medium.

Another subject of the present invention is a structured composition for at least one keratinous material comprising at least one dyestuff and at least one continuous liquid fatty phase, wherein said at least one continuous liquid fatty phase is structured with a sufficient amount of at least one structuring polymer which has a weight-average molecular mass ranging up to 30,000 and which comprises a) a polymeric skeleton comprising repeating units comprising at least one hetero atom, and b) at least one fatty chain, optionally functionalized, comprising from 12 to 120 carbon atoms, chosen from pendant fatty chains and terminal fatty chains which are bonded to the polymeric skeleton, wherein the at least one fatty chain is present in a quantity ranging from 40% to 98% of the total number of all the repeating units comprising at least one hetero atom and all the at least one fatty chain, wherein the composition being in the form of a wax-free solid which may be a self-supporting solid and having a hardness ranging from 20 g to 2000 g, and wherein the at least one dyestuff, the at least one continuous liquid fatty phase and the at least one structuring polymer form a physiologically acceptable medium. In one embodiment of the present invention, the composition has a hardness ranging from 20 g to 900 g. In another embodiment, the composition has a hardness ranging from 20 g to 600 g.

In one embodiment of the present invention, the composition comprises at least one structuring polymer which has a weight-average molecular mass ranging from 1000 to 10,000. In another embodiment, the at least one structuring polymer has a weight-average molecular mass ranging from 2000 to 8000. This at least one structuring polymer may be a solid which is undeformable at room temperature (25° C.) and atmospheric pressure (760 mmHg). Additionally, this at least one structuring polymer may be capable of structuring the composition without opacifying it.

According to the present invention, the at least one structuring polymer comprises at least one fatty chain, optionally functionalized. As used herein, "polymer" means a compound comprising at least two repeating units. As used herein, "repeating units" of the polymer are hydrocarbon-based repeating units, wherein each unit comprises from 2 to 80 carbon atoms wherein the carbon atoms are substituted with hydrogen atoms and may optionally be substituted with oxygen atoms, and wherein the hydrocarbons may be linear, branched or cyclic, and saturated or unsaturated. In one embodiment of the present invention, the hydrocarbon-based repeating units comprise from 2 to 60 carbon atoms. The repeating units of the polymer, also called chain members, may each also comprise at least one hetero atom within the polymeric skeleton. As will be explained further below, these hydrocarbon-based repeating units can, for example, also contain amide groups.

As used herein, "functionalized" means comprising one or more functional groups. Non-limiting examples of functional groups include hydroxyl groups, ether groups, oxyalkylene groups, polyoxyalkylene groups, carboxylic acid groups, amine groups, halogen atoms, ester groups, siloxane groups and polysiloxane groups. The expression "functionalized chain" means an alkyl chain comprising at least one functional (reactive) group chosen from those recited above.

In addition, the hydrogen atoms of the at least one fatty chain can be at least partially substituted with fluorine atoms.

In one embodiment of the present invention, the at least one fatty chain of the at least one structuring polymer is present in a quantity ranging from 40% to 98% of the total number of all the repeating units comprising at least one hetero atom and all the at least one fatty chains. In another embodiment, the at least one fatty chain of the at least one structuring polymer is present in a quantity ranging from 50% to 95% of the total number of all the repeating units comprising at least one hetero atom and all the at least one fatty chains.

The nature and proportion of the repeating units comprising at least one hetero atom will depend on the desired nature of the at least one continuous liquid fatty phase. Thus, the nature of the at least one continuous liquid fatty phase may be similar to the nature of the repeating units comprising at least one hetero atom. This may be so because increasing the proportion of the repeating units comprising at least one hetero atom and their polarity (which corresponds to the number and nature of the hetero atoms) will increase the affinity of the at least one structuring polymer for polar oils. On the other hand, if the at least one structuring polymer comprises repeating units which are of low polarity or are apolar, the at least one structuring polymer will have a proportionately greater affinity for apolar oils.

In one embodiment of the present invention, the at least one hetero atom of the repeating units (chain members)

comprising at least one hetero atom discussed above is chosen from nitrogen atoms, sulfur atoms and phosphorus atoms and may optionally be substituted with at least one oxygen atom. In another embodiment, the repeating units comprising at least one hetero atom comprise at least one polar group of carbonyl type. In yet another embodiment, the repeating units comprising at least one hetero atom are chosen from repeating units comprising at least one non-pendant hetero atom.

In one embodiment of the present invention, the repeating units comprising at least one non-pendant hetero atom are chosen from repeating units comprising hydrocarbon-based repeating units, silicone units which form a polyorganosiloxane-type skeleton, repeating units comprising amide units which form a polyamide-type skeleton, repeating units comprising units which comprise isocyanate groups which form a skeleton chosen from polyurethane-type skeleton, polyurea-type skeleton and polyureaurethane-type skeleton, repeating units comprising carbamate which form a skeleton chosen from polyurethane-type skeleton, polyurea-type skeleton and polyureaurethane-type skeleton, and repeating units comprising urea which form a skeleton chosen from polyurethane-type skeleton, polyurea-type skeleton and polyureaurethane-type skeleton. In another embodiment of the present invention, the repeating units are chosen from repeating units comprising amide units. In another embodiment, the at least one fatty chain is chosen from pendant fatty chains and is bonded directly to at least one of the hetero atoms of the polymeric skeleton. In another embodiment, the at least one structuring polymer further comprises oxyalkylene units between the repeating units.

In one embodiment, the compositions comprise at least one structuring polymer comprising a polymeric skeleton which comprises polyamide-type repeating units and at least one fatty chain comprising from 12 to 120 carbon atoms, wherein said at least one fatty chain is chosen from terminal fatty chains, if present, is bonded to the polyamide skeleton via ester functions. In another embodiment, said at least one fatty chain comprises from 12 to 68 carbon atoms.

In one embodiment, the at least one structuring polymer is chosen from polymers resulting from at least one polycondensation reaction between at least one dicarboxylic acid comprising at least 32 carbon atoms, such as from 32 to 44 carbon atoms, with at least one diamine comprising at least 2 carbon atoms, such as from 2 to 36 carbon atoms. The at least one dicarboxylic acid can, for example, be chosen from dimers of at least one fatty acid comprising at least 16 carbon atoms, such as oleic acid, linoleic acid and linolenic acid. The at least one diamine can, for example, be chosen from ethylenediamine, hexylenediamine, hexamethylenediamine, phenylenediamine and ethylenetriamine.

In one embodiment, the at least one structuring polymer is chosen from polymers comprising one or two terminal carboxylic acid groups. The terminal carboxylic acid groups can, for example, be esterified with at least one alcohol chosen from monoalcohols comprising at least 4 carbon atoms. For example, the at least one alcohol can be chosen from monoalcohols comprising from 10 to 36 carbon atoms. In a further example, the monoalcohols can comprise from 12 to 24 carbon atoms, while in yet another example, they can from 16 to 24 carbon atoms.

In one embodiment of the present invention, the at least one structuring polymer is chosen from those described in document U.S. Pat. No. 5,783,657 from the company Union Camp, the disclosure of which is incorporated by reference, which are polymers of formula (I):

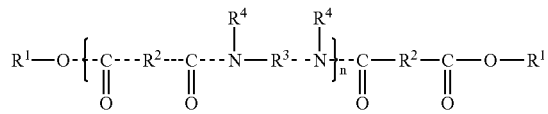

in which:
n is an integer which represents the number of amide units such that the number of ester groups present in said at least one structuring polymer ranges from 10% to 50% of the total number of all said ester groups and all said amide groups comprised in said at least one structuring polymer;

$R^1$, which are identical or different, are each chosen from alkyl groups comprising at least 4 carbon atoms and alkenyl groups comprising at least 4 carbon atoms;

$R^2$, which are identical or different, are each chosen from $C_4$ to $C_{42}$ hydrocarbon-based groups with the proviso that at least 50% of $R^2$ are chosen from $C_{30}$ to $C_{42}$ hydrocarbon-based groups;

$R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and $R^4$, which are identical or different, are each chosen from hydrogen atoms, $C_1$ to $C_{10}$ alkyl groups and a direct bond to group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms. The at least one structuring polymer chosen from polymers of formula (I) may comprise terminal fatty chains, optionally functionalized, which are bonded to the last hetero atom of the polymeric, such as polyamide, skeleton.

The ester groups of the at least one structuring polymer of formula (I) which form part of the at least one fatty chain, the fatty chain being terminal and/or pendant, can be present in a proportion ranging from 15% to 40% of the total number of all ester and amide groups in the at least one structuring polymer, such as from 20% to 35% of the total number of all ester and amide groups in the at least one structuring polymer.

In the present invention, n can be an integer ranging from 1 to 5. In the present invention, $R^1$, which are identical or different, can each be chosen from $C_{12}$ to $C_{22}$ alkyl groups, such as from $C_{16}$ to $C_{22}$ alkyl groups.

In the present invention, $R^2$, which are identical or different, can each be chosen from $C_{10}$ to $C_{42}$ alkyl groups. At least 50% of $R^2$, which are identical or different, can each be chosen from groups comprising from 30 to 42 carbon atoms. At least 75% of $R^2$, which are identical or different, can each be chosen from groups comprising from 30 to 42 carbon atoms. In the two aforementioned embodiments, the remaining $R^2$, which are identical or different, are each chosen from $C_4$ to $C_{19}$ groups, or $C_4$ to $C_{12}$ groups.

$R^3$, which can be identical or different, can each be chosen from $C_2$ to $C_{36}$ hydrocarbon-based groups and polyoxyalkylene groups. In another embodiment, $R^3$, which are identical or different, are each chosen from $C_2$ to $C_{12}$ hydrocarbon-based groups. In another embodiment, R₄, which are identical or different, are each chosen from hydrogen atoms. As used herein, hydrocarbon-based groups may be linear, cyclic or branched and saturated or unsaturated. As is clear the hydrocarbon-based groups can be aliphatic or aromatic.

According to the present invention, structuring of the at least one continuous liquid fatty phase may be obtained with the aid of at least one structuring polymer of formula (I). The at least one structuring polymer of formula (I) may, of course, be in the form of mixtures of polymers, and these mixtures may also comprise a compound of formula (I) wherein n is equal zero, i.e. a diester.

Non-limiting examples of at least one structuring polymer which may be used in the composition according to the present include the commercial products sold by the Bush Boake Allen Co. under the names Uniclear 80 and Uniclear 100. These are sold, respectively, in the form of an 80% (in terms of active material) gel in a mineral oil and a 100% (in terms of active material) gel. These polymers have a softening point ranging from 88° C. to 94° C., and may be mixtures of copolymers derived from monomers of (i) $C_{36}$ diacids and (ii) ethylenediamine, and have a weight-average molecular mass of about 6000. Terminal ester groups result from esterification of the remaining acid end groups with at least one alcohol chosen from cetyl alcohol and stearyl alcohol. A mixture of cetyl and stearyl alcohols is sometimes called cetylstearyl alcohol.

In one embodiment of the present invention, the at least one structuring polymer has a softening point greater than 70° C., such as from 70° C. to 190° C. and further such as from 80° C. to 130° C., and even further such as from 80° C. to 105° C. This softening point may be lower than that of structuring polymers known in the art which may facilitate the use of the at least one structuring polymer of the present invention and may limit the degradation of the continuous liquid fatty phase.

Due to the at least one fatty chain, the at least one structuring polymer of the present invention may have good solubility in oils (i.e. water-immiscible liquid compounds) and thus may give macroscopically homogeneous compositions, even with a high (at least 25%) content of the at least one structuring polymer, unlike certain polymers of the prior art that do not comprise a fatty chain.

The composition may further comprise at least one amphiphilic compound which is liquid at room temperature and which has a hydrophilic/lipophilic balance (HLB) value of less than 12, such as from 1 to 7, further such as from 1 to 5, and even further such as from 3 to 5. According to the present invention, at least one amphiphilic compound may be used. These amphiphilic compounds may reinforce the structuring properties of the at least one structuring polymer which comprises a polymeric skeleton comprising repeating units comprising at least one hetero atom, may facilitate the use of the at least one structuring polymer and may also improve the depositability of the stick.

The composition of the present invention may have a hardness ranging from 20 g to 2000 g, such as from 20 g to 900 g, and further such as from 20 g to 600 g. This hardness may be measured according to a method of penetrating a probe into said composition and in particular using a texture analyzer (for example TA-XT2 from Rhéo) equipped with an ebonite cylinder of height 25 mm and diameter 8 mm. The hardness measurement is carried out at 20° C. at the center of 5 samples of said composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 g.

The hardness may also be measured by a "cheese wire" method, which involves cutting an 8.1 mm tube of lip composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may range from 30 g to 150 g, such as from 30 g to 120 g, and further such as from 30 g to 50 g.

The hardness of the composition of the present invention may be such that the compositions are self-supporting and can easily disintegrate to form a satisfactory deposit on a keratinous material. In addition, this hardness may impart good impact strength to the inventive compositions.

According to the present invention, the compositions in stick form may possess the properties of deformable, flexible elastic solids and may have noteworthy elastic softness upon application on a keratinous material. The compositions in stick form of the prior art may not have this elasticity and flexibility.

At least one amphiphilic compound is chosen from amphiphilic compounds which comprise at least one lipophilic part bonded to at least one polar part. For example, the at least one lipophilic part may comprise a carbon-based chain comprising at least 8 carbon atoms, such as from 18 to 32 carbon atoms and further such as from 18 to 28 carbon atoms.

The at least one polar part, for example, may be chosen from compounds derived from alcohols comprising from 1 to 12 hydroxyl groups, polyols comprising from 2 to 12 hydroxyl groups, and polyoxyalkylenes comprising at least 2 oxyalkylene units. For example, the polyoxyalkylenes comprising at least 2 oxyalkylene units may be chosen from polyoxyalkylenes comprising from 0 to 20 oxypropylene units and from 0 to 20 oxyethylene units.

For example, the at least one amphiphilic compound may be chosen from esters, such as from monoesters and diesters. Representative esters are chosen from hydroxystearates of glycerol, oleates of glycerol, isostearates of glycerol, hydroxystearates of sorbitan, oleates of sorbitan, isostearates of sorbitan, hydroxystearates of methylglucose, oleates of methylglucose, isostearates of methylglucose, hydroxystearates of branched $C_{12}$ to $C_{26}$ fatty alcohols, oleates of branched $C_{12}$ to $C_{26}$ fatty alcohols and isostearates of branched $C_{12}$ to $C_{26}$ fatty alcohols, such as octyldodecanols.

The concentrations of the at least one amphiphilic compound and of the at least one structuring polymer are chosen according to the desired hardness of the compositions and according to the specific application envisaged. The respective concentrations of the at least one structuring polymer and of the at least one amphiphilic compound can be such that the composition can be in the form of a stick which can be worn down. For example, the at least one structuring polymer (as active material) can be present in a concentration ranging from 0.5% to 80% by weight of the total weight of the composition, such as from 5% to 40% by weight of the total weight of the composition. For example, the at least one amphiphilic compound can be present in a concentration ranging from 0.1% to 35% by weight of the total weight of the composition, such as from 2% to 15% by weight of the total weight of the composition.

For example, the at least one continuous liquid fatty phase can comprise greater than 40% by weight of the total weight of the continuous liquid fatty phase of at least one liquid oil comprising a group similar to that of the repeating units comprising at least one hetero atom, such as greater than 50% by weight.

A non-limiting example includes at least one continuous liquid fatty phase structured with a sufficient amount of at least one structuring polymer which comprises a polyamide-type skeleton wherein the at least one continuous liquid fatty phase comprises greater than 50% by weight of the total weight of the at least one continuous liquid fatty phase of at least one apolar liquid oil, such as a hydrocarbon-based oil with amide repeating units. Another non-limiting example includes at least one continuous liquid fatty phase structured with a sufficient amount of at least one structuring polymer which comprises a partially silicone-based skeleton, wherein the at least one fatty phase comprises greater than 40%, such as greater than 50% by weight of the total weight of the at least one continuous liquid fatty phase of at least one silicone-based liquid oil. Another non-limiting example includes at least one continuous liquid fatty phase structured with a sufficient amount of at least one apolar polymer of the hydrocarbon-based type, wherein the at least one fatty phase comprises greater than 40%, such as greater than 50% by weight of the total weight of the at least one continuous liquid fatty phase of at least one apolar oil such as a hydrocarbon-based oil.

Representative polar oils of the present invention may be chosen from:
  hydrocarbon-based plant oils having a high content of triglycerides chosen from fatty acid esters of glycerol in which the fatty acids may have varied chain lengths, these chains may be chosen from linear, branched, cyclic, saturated and unsaturated chains. Non-limiting examples of these oils are wheat germ oil, corn oil, sunflower oil, karite butter, castor oil, sweet almond oil, macadamia oil, apricot oil, soybean oil, rape seed oil, cotton oil, alfalfa oil, poppy oil, pumpkin oil, sesame oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil, musk rose oil and caprylic/capric acid triglycerides such as those sold by Stearineries Dubois Co. and those sold under the names Miglyol 810, 812 and 818 by Dynamit Nobel Co.;
  synthetic oils and esters of formula $R_5COOR_6$ in which $R_5$ is chosen from linear and branched higher fatty acid groups comprising from 1 to 40 carbon atoms, such as from 7 to 19 carbon atoms; and $R_6$ is chosen from branched hydrocarbon-based groups comprising from 1 to 40 carbon atoms, such as from 3 to 20 carbon atoms, with the proviso that the total number of carbon atoms in $R_5$ and $R_6$ is greater than or equal to 10, such as, for example, in purcellin oil (cetostearyl octanoate), isononyl isononanoate, $C_{12}$–$C_{15}$ alkyl benzoates, isopropyl myristate, 2-ethylhexyl palmitate, alkyl octanoates, polyalkyl octanoates, decanoates ricinoleates, hydroxylated esters such as isostearyl lactate and diisostearyl malate, and pentaerythritol esters;
  synthetic ethers comprising from 10 to 40 carbon atoms; and
  $C_8$ to $C_{26}$ fatty alcohols such as oleyl alcohols.

Representative apolar oils according to the present invention may be chosen from silicone oils such as volatile and nonvolatile, linear, branched and cyclic polydimethylsiloxanes (PDMSs) that are liquid at room temperature; polydimethylsiloxanes comprising groups chosen from alkyl groups, alkoxy groups and phenyl groups, optionally pendant or terminal, and each comprising from 2 to 24 carbon atoms; phenylsilicones such as phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates; linear, branched and cyclic, volatile and nonvolatile hydrocarbons and fluorocarbons of synthetic and mineral origin, such as volatile liquid paraffins (such as isoparaffins and isododecane), nonvolatile liquid paraffins and derivatives thereof, petroleum jelly, polydecenes, hydrogenated polyisobutene such as parleam, and squalane.

The at least one structured oil, such as those structured with a sufficient amount of at least one structuring polymer chosen from polyamides such as those of formula (I), polyurethanes, polyureas and polyurea-polyurethanes, may be apolar oils of the hydrocarbon-based type of mineral or synthetic origin, and may be chosen from hydrocarbons such as alkanes comprising parleam oil, isoparaffins such as isododecane and squalane.

In one embodiment, the at least one continuous liquid fatty phase is present in a concentration ranging from 5% to 99% by weight of the total weight of the composition, such as from 20% to 75%.

The composition of the present invention may further comprise at least one suitable additive commonly used in the field concerned chosen from water optionally thickened or gelled with an aqueous-phase thickener or gelling agent, antioxidants, essential oils, preserving agents, fragrances, neutralizing agents, liposoluble polymers, and cosmetically active agents and dermatological active agents such as, for example, emollients, moisturizers, vitamins, essential fatty acids and sunscreens. The at least one additive is generally present in a concentration ranging from 0% to 20% by weight of the total weight of the composition, such as from 0% to 10%. The at least one additive can be broadly chosen from cosmetically active agents and dermatologically active agents.

Needless to say, the person skilled in the art will take care to select the optional additional additives and the amount thereof such that the advantageous properties of the composition according to the invention are not, or are not substantially, adversely affected by the addition(s) envisaged.

The present invention may be directed to a dermatological composition, such as a tinted composition, for at least one keratin material, such as the skin, the lips and superficial body growths, a care composition for at least one keratin material, a make-up composition, a body hygiene composition, a sunscreen composition for at least one keratin material, or an after-sun composition for at least one keratin material comprising a composition comprising (a) at least one dyestuff and (b) at least one continuous liquid fatty phase, wherein said at least one continuous liquid fatty phase is structured with a sufficient amount of at least one structuring polymer which has a weight-average molecular mass ranging up to 30,000 and which comprises a) a polymeric skeleton comprising repeating units comprising at least one hetero atom, and b) at least one fatty chain, optionally functionalized, comprising from 12 to 120 carbon atoms, chosen from pendant fatty chains and terminal fatty chains which are bonded to said polymeric skeleton, wherein said at least one fatty chain is present in a quantity ranging from 40% to 98% of the total number of all said repeating units comprising at least one hetero atom and all said at least one fatty chains, and wherein said composition is in the form of a solid. The present invention may also be wax-free. The present invention may also comprise a body hygiene composition chosen from deodorant products and make-up-removing products. The present invention may be in the form of a stick. The composition of the present invention may be used as a care base for at least one keratinous material such as the skin, superficial body growths or the lips. Non-limiting examples include lip balms for protecting the lips against cold, sunlight or wind and creams for skin, nails or hair. Further, the repeating units comprising at least one hetero atom can be chosen from repeating units comprising at least one non-pendant hetero atom.

The present invention is also directed to a make-up composition for at least one keratinous material comprising (a) at least one dyestuff, and (b) at least one continuous liquid fatty phase, wherein said at least one continuous liquid fatty phase is structured with a sufficient amount of at least one structuring polymer which has a weight-average molecular mass ranging up to 30,000 and which comprises a) a polymeric skeleton comprising repeating units comprising at least one hetero atom and b) at least one fatty chain, optionally functionalized, comprising from 12 to 120 carbon atoms, chosen from pendant fatty chains and terminal fatty chains which are bonded to said polymeric skeleton, wherein said at least one fatty chain is present in a quantity ranging from 40% to 98% of the total number of all said repeating units comprising at least one hetero atom and all said at least one fatty chains, and wherein said composition is in the form of a wax-free solid. For example, the composition can be in the form of a colored make-up product for the skin, such as a foundation, optionally having care or treating properties, a blusher, a face powder, an eyeshadow, a concealer product, an eyeliner or a make-up product for the body; a lip make-up such as a lipstick, optionally having care or treating properties; a make-up product for superficial body growths, such as nails or eyelashes, in particular in the form of a tablet of mascara, or for the eyebrows and the hair, such as in the form of a pencil. As is clear, the composition can be in the form of a stick, a pencil, a tablet or a dish. The composition may be a cosmetic product broadly further comprising at least one suitable additive chosen from cosmetically active agents and dermatologically active agents. Further, the repeating units comprising at least one hetero atom can be chosen from repeating units comprising at least one non-pendant hetero atom.

Needless to say, the composition of the invention should be cosmetically and/or dermatologically acceptable, that is, it should comprise a nontoxic, physiologically acceptable medium which can be applied to at least one human keratinous material. As used herein, "cosmetically acceptable" means having a pleasant appearance, odor and feel.

The at least one dyestuff is representatively chosen from the lipophilic dyes, hydrophilic dyes, pigments and nacres. As used herein, "pigment" means any solid particle which is insoluble in the medium and which serves any of the functions chosen from giving a color, modifying a color, giving an iridescent appearance and modifying an iridescent appearance. The at least one dyestuff is generally present in a concentration ranging from 0.01% to 40% by weight relative to the total weight of said composition, such as from 1% to 35%, and further such as from 5% to 25%.

The at least one dyestuff may be chosen from pigments and nacres in order to obtain make-up compositions which give good coverage, that is, which do not leave a significant amount of the at least one keratin material to which it is applied showing through. The pigments may also reduce the sticky feel of the compositions, unlike soluble dyes.

Representative liposoluble dyes which may be used according to the present invention include Sudan red, DC Red 17, DC Green 6, β-carotene, soybean oil, Sudan brown, DC Yellow 11, DC Violet 2, DC Orange 5 and quinoline yellow. The liposoluble dyes, when present, generally have a concentration ranging up to 20% by weight of the total weight of the composition, such as from 0.1% to 6%.

The pigments which may be used according to the present invention may be chosen from white, colored, mineral, organic, coated and uncoated pigments. Representative examples of mineral pigments include titanium dioxide, optionally surface-treated, zirconium oxide, cerium oxide, iron oxides, chromium oxides, manganese violet, ultramarine blue, chromium hydrate and ferric blue. Representative examples of organic pigments include carbon black, pigments of D & C type, and lakes based on cochineal carmine, barium, strontium, calcium and aluminum. If present, the pigments may have a concentration ranging up to 40% by weight of the total weight of the composition, such as from 1% to 35%, and further such as from 2% to 25%.

The nacreous pigments (or nacres) which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacres, if present, may have a concentration ranging up to 20% by weight of the total weight of the composition, such as from 0.1% to 15%.

The compositions according to the present invention may be manufactured by one of ordinary skill in the art. For example, they may be manufactured by a process which comprises heating the at least one structuring polymer at least to its softening point, adding the at least one amphiphilic compound, if present, the at least one dyestuff and the at least one suitable additive, if present, to the at least one structuring polymer followed by mixing the composition until a clear, transparent solution is obtained. The resultant homogeneous mixture may then be cast in a suitable mold such as a lipstick mold or cast directly into the packaging articles such as a case or a dish.

The present invention is also directed to a cosmetic process for caring for, making up or treating a keratin material, such as that of a human being, and further such as human skin, comprising the application to a keratin material of a cosmetic composition comprising (a) at least one pigment in an amount sufficient to make up the skin, the lips and/or superficial body growths, and (b) at least one continuous liquid fatty phase, wherein said at least one continuous liquid fatty phase is structured with a sufficient amount of at least one structuring polymer which has a weight-average molecular mass ranging up to 30,000 and which comprises a) a polymeric skeleton comprising repeating units comprising at least one hetero atom, and b) at least one fatty chain, optionally functionalized, comprising from 12 to 120 carbon atoms, chosen from pendant fatty chains and terminal fatty chains which are bonded to said polymeric skeleton, wherein said at least one fatty chain is present in a quantity ranging from 40% to 98% of the total number of all said repeating units comprising at least one hetero atom and all said at least one fatty chains, and wherein said at least one pigment, at least in some embodiments, said at least one continuous liquid fatty phase and said at least one structuring polymer form a physiologically acceptable medium. The composition can be applied in this process in the form of a structured solid. The composition applied in this process can also be wax-free. The composition applied in this process can also have a hardness ranging from 20 g to 2000 g, such as from 20 g to 900 g, and further such as from 20 g to 600 g. Further, the repeating units comprising at least one hetero atom can be chosen from repeating units comprising at least one non-pendant hetero atom.

The present invention is also directed to a process of structuring a composition in the form of a self-supporting solid having a hardness ranging from 20 g to 2000 g, such as from 20 g to 900 g, and further such as from 20 g to 600 g, comprising the step of including in said composition a sufficient amount of at least one structuring polymer which has a weight-average molecular mass ranging up to 30,000 and which comprises a) a polymeric skeleton comprising repeating units comprising at least one hetero atom, and b) at least one fatty chain, optionally functionalized, comprising from 12 to 120 carbon atoms, chosen from pendant fatty chains and terminal fatty chains which are bonded to said polymeric skeleton, wherein said at least one fatty chain is present in a quantity ranging from 40% to 98% of the total number of all said repeating units comprising at least one hetero atom and all said at least one fatty chains, said composition being structured as a self-supporting solid, being wax-free and further containing at least one continuous liquid fatty phase and at least one dyestuff. The repeating units comprising at least one hetero atom can be chosen from repeating units comprising at least one non-pendant hetero atom.

For example, the at least one structuring polymer of the composition structured from this process can be chosen from polyamides. The at least one structuring polymer of the composition structured from this process can also have a weight-average molecular mass ranging from 1000 to 10,000. The at least one structuring polymer of the composition structured from this process can also be chosen from polyamides comprising end groups which comprise at least one ester functional group comprising at least one hydrocarbon-based chain which comprises from 10 to 42 carbon atoms. The at least one structuring polymer of the composition structured from this process can also be combined with at least one amphiphilic compound that is liquid at room temperature, with an HLB value of less than 12, such as from 1 to 7, and further such as from 1 to 5.

The present invention is also directed to a process of structuring a cosmetic composition in the form of a physiologically acceptable composition, which is rigid, self-supporting, wax-free, glossy and/or non-migrating comprising including in said composition at least one continuous liquid fatty phase, wherein said at least one continuous liquid fatty phase is structured with a sufficient amount of at least one structuring polymer which has a weight-average molecular mass ranging up to 30,000 and which comprises a) a polymeric skeleton comprising repeating units comprising at least one hetero atom, and b) at least one fatty chain, optionally functionalized, comprising from 12 to 120 carbon atoms, chosen from pendant fatty chains and terminal fatty chains which are bonded to said polymeric skeleton, wherein said at least one fatty chain is present in a quantity ranging from 40% to 98% of the total number of all said repeating units comprising at least one hetero atom and all said at least one fatty chains; and wherein said composition is rigid, self-supporting, wax-free, glossy and/or non-migrating.

In the present invention, the repeating units comprising at least one hetero atom can be chosen from repeating units comprising at least one non-pendant hetero atom. For example, the at least one structuring polymer of the composition structured from this process can be chosen from polyamides. The at least one structuring polymer of the composition structured from this process can also be chosen from polyamides comprising end groups which comprise at least one ester functional group comprising at least one hydrocarbon-based chain which comprises from 10 to 42 carbon atoms. The at least one structuring polymer of the composition structured from this process can also be combined with at least one amphiphilic compound that is liquid at room temperature, with an HLB value of less than 12, such as from 1 to 7, and further such as from 1 to 5.

The present invention is also directed to a process of making a cosmetic composition in the form of a physiologically acceptable composition, which is structured, rigid, self-supporting, wax-free, glossy and/or non-migrating comprising including in said composition at least one continuous liquid fatty phase, said at least one continuous liquid fatty phase being structured with a sufficient amount of at least one structuring polymer which has a weight-average molecular mass ranging up to 30,000 and which comprises a) a polymeric skeleton comprising repeating units comprising at least one hetero atom, and b) at least one fatty chain, optionally functionalized, comprising from 12 to 120 carbon atoms, chosen from pendant fatty chains and terminal fatty chains which are bonded to said polymeric skeleton, wherein said at least one fatty chain is present in a quantity ranging from 40% to 98% of the total number of all said repeating units comprising at least one hetero atom and all said at least one fatty chains; and wherein said composition is rigid, self-supporting, wax-free, glossy and/or non-migrating.

The repeating units comprising at least one hetero atom can be chosen from repeating units comprising at least one non-pendant hetero atom. For example, the at least one structuring polymer of the composition made from this process can be chosen from polyamides. The at least one structuring polymer of the composition made from this process can also be chosen from polyamides comprising end groups which comprise at least one ester functional group comprising at least one hydrocarbon-based chain which comprises from 10 to 42 carbon atoms. The at least one structuring polymer of the composition made from this process can also be combined with at least one amphiphilic compound that is liquid at room temperature, with an HLB value of less than 12, such as from 1 to 7, and further such as from 1 to 5.

The present invention is also directed to a process of structuring a cosmetic composition in the form of a self-supporting solid, comprising including in said composition at least one continuous liquid fatty phase and at least one dyestuff, wherein said at least one continuous liquid fatty phase and said at least one dyestuff are structured with a sufficient amount of at least one structuring polymer which has a weight-average molecular mass ranging up to 30,000 and which comprises a) a polymeric skeleton comprising repeating units comprising at least one hetero atom, and b) at least one fatty chain, optionally functionalized, comprising from 12 to 120 carbon atoms, chosen from pendant fatty chains and terminal fatty chains which are bonded to said polymeric skeleton, wherein said at least one fatty chain is present in a quantity ranging from 40% to 98% of the total number of all said repeating units comprising at least one hetero atom and all said at least one fatty chains; and wherein said composition is in the form of a self-supporting solid. Further, the repeating units comprising at least one hetero atom can be chosen from repeating units comprising at least one non-pendant hetero atom.

The present invention is also directed to a process for limiting the migration of a cosmetic composition comprising including in said composition at least one continuous liquid fatty phase, wherein said at least one continuous liquid fatty phase is structured with a sufficient amount of an agent for limiting the migration of said composition, said agent comprising at least one structuring polymer which has a weight-average molecular mass ranging up to 30,000 and which comprises a) a polymeric skeleton comprising repeating units comprising at least one hetero atom, and b) at least one fatty chain, optionally functionalized, comprising from 12 to 120 carbon atoms, chosen from pendant fatty chains and terminal fatty chains which are bonded to said polymeric skeleton, wherein said at least one fatty chain is present in a quantity ranging from 40% to 98% of the total number of all said repeating units comprising at least one hetero atom and all said at least one fatty chains.

The cosmetic composition that this process limits the migration of has a hardness ranging from 20 g to 2000 g, such as from 20 g to 900 g, and further such as from 20 g to 600 g. Further, the repeating units comprising at least one hetero atom can be chosen from repeating units comprising at least one non-pendant hetero atom.

The present invention is also directed to a process for limiting the migration of a cosmetic composition comprising at least one continuous liquid fatty phase comprising structuring said at least one continuous fatty phase with a sufficient amount of structuring polymer which has a weight-average molecular mass ranging up to 30,000 and which comprises a) a polymeric skeleton comprising repeating units comprising at least one hetero atom, and b) at least one fatty chain, optionally functionalized, comprising from 12 to 120 carbon atoms, chosen from pendant fatty chains and terminal fatty chains which are bonded to said polymeric skeleton, and wherein said at least one fatty chain is present in a quantity ranging from 40% to 98% of the total number of all said repeating units comprising at least one hetero atom and all said at least one fatty chains. In one embodiment, the repeating units comprising at least one hetero atom are chosen from repeating units comprising at least one non-pendant hetero atom.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result. The percentages are given on a weight basis.

EXAMPLE 1

Lip Composition

| | |
|---|---|
| Uniclear 80 | 25.0% |
| Parleam oil | 56.0% |
| Polyglyceryl-2 polyhydroxystearate | 10.0% |
| Pigments (brown iron oxide + titanium oxide) | 9.0% |

Preparation: the Uniclear 80 was solubilized (or dissolved) with the aid of the polyglyceryl-2 polyhydroxystearate in the parleam oil, at 100° C., followed by addition of the pigments. The whole was mixed using a deflocculating turbomixer (Rayneri) and then cast in lipstick molds.

A stick of lip composition having a hardness of 425 g, measured using a TA-XT2 texture analyzer at 20° C., was obtained. The lip composition obtained was glossy and non-migrating. This was confirmed by a test with a panel of experts, by comparison with a glossy product of the prior art: Rouge Absolu from Lancôme. The lip composition of the invention was considered by all of the testers as being glossier when applied than the lip composition of the prior art, and as migrating less after being worn for 2 hours.

EXAMPLE 2

Anhydrous eyeshadow

| | | |
|---|---|---|
| Uniclear 80 | | 25.0% |
| Parleam oil | | 35.1% |
| Glyceryl oleate | | 31.25% |
| Pigments | qs | 100% |

This eyeshadow in stick form was prepared as in Example 1. It was glossy and non-migrating.

EXAMPLE 3

Lip composition

The product differs from Example 1 by the use of Uniclear 100 instead of Uniclear 80.

COUNTEREXAMPLE

The lip composition Example 1 was repeated, replacing the Uniclear 80 polyamide with the Versamid® 930 polyamide sold by the company Henkel, and then by the Macromelt® 6212 polyamide also sold by the company Henkel, these two polyamides being free of an end group with an alkyl or alkenyl chain comprising at least 4 carbon atoms, linked to the polyamide skeleton via an ester group.

The products obtained were totally heterogeneous and in two-phase form. They did not in any way have the appearance or hardness of a stick.

What is claimed is:

1. A structured cosmetic composition comprising:
(i) at least one continuous liquid fatty phase,
wherein said at least one continuous liquid fatty phase is structured with a sufficient amount of at least one polymer of formula (I) and mixtures thereof:

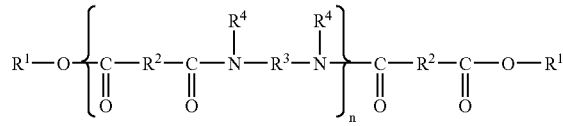

in which:
n is an integer which represents the number of amide units such that the number of ester groups present in said at least one structuring polymer ranges from 10% to 50% of the total number of all said ester groups and all said amide groups comprised in said at least one structuring polymer;
$R^1$, which are identical or different, are each chosen from alkyl groups comprising at least 4 carbon atoms and alkenyl groups comprising at least 4 carbon atoms;
$R^2$, which are identical or different, are each chosen from $C_4$ to $C_{42}$ hydrocarbon-based groups with the proviso that at least 50% of $R^2$ are chosen from $C_{30}$ to $C_{42}$ hydrocarbon-based groups;
$R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and
$R^4$, which are identical or different, are each chosen from hydrogen atoms, $C_1$ to $C_{10}$ alkyl groups and a direct bond to group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms;
(ii) at least one amphiphilic compound chosen from amphiphilic compounds which are liquid at room temperature and have an HLB value of less than 12; and
(iii) at least one dyestuff,
wherein said structured composition is in the form of a non-migrating, wax-free solid, and
wherein said at least one continuous liquid fatty phase, said at least one polymer, said at least one amphiphilic compound, and said at least one dyestuff form a physiologically acceptable medium.

2. A composition according to claim 1, wherein said HLB value ranges from 1 to 7.

3. A composition according to claim 2, wherein said HLB value ranges from 1 to 5.

4. A process of structuring a cosmetic composition in the form of a physiologically acceptable composition, which is wax-free and non-migrating comprising including in said composition
(i) at least one liquid continuous fatty phase, said at least one liquid continuous fatty phase being structured with a sufficient amount of at least one polymer of formula (I) and mixtures thereof:

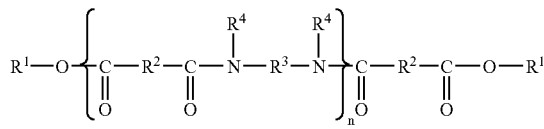

in which:
n is an integer which represents the number of amide units such that the number of ester groups present in said at least one structuring polymer ranges from 10% to 50% of the total number of all said ester groups and all said amide groups comprised in said at least one structuring polymer;
$R^1$, which are identical or different, are each chosen from alkyl groups comprising at least 4 carbon atoms and alkenyl groups comprising at least 4 carbon atoms;
$R^2$, which are identical or different, are each chosen from $C_4$ to $C_{42}$ hydrocarbon-based groups with the proviso that at least 50% of $R^2$ are chosen from $C_{30}$ to $C_{42}$ hydrocarbon-based groups;
$R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and
$R^4$, which are identical or different, are each chosen from hydrogen atoms, $C_1$ to $C_{10}$ alkyl groups and a direct bond to group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms;
(ii) at least one amphiphilic compound chosen from amphiphilic compounds which are liquid at room temperature and have an HLB value of less than 12; and
(iii) at least one dyestuff,
wherein said composition is wax-free and non-migrating.

5. A process according to claim 4, wherein said HLB value ranges from 1 to 7.

6. A process according to claim 5, wherein said HLB value ranges from 1 to 5.

7. A structured cosmetic composition comprising:
(i) at least one continuous liquid fatty phase, wherein said at least one continuous liquid fatty phase is structured with a sufficient amount of at least one polymer chosen from ethylenediamine/stearyl dimer tallate copolymer;
(ii) at least one amphiphilic compound chosen from amphiphilic compounds which are liquid at room temperature and have an HLB value of less than 12; and
(iii) at least one dyestuff;
wherein said structured composition is in the form of a non-migrating, wax-free solid, and
wherein said at least one continuous liquid fatty phase, said at least one polymer, said at least one amphiphilic compound, and said at least one dyestuff form a physiologically acceptable medium.

8. A process of structuring a cosmetic composition in the form of a physiologically acceptable composition, which is wax-free and non-migrating comprising including in said composition:
(i) at least one liquid continuous fatty phase, said at least one liquid continuous fatty phase being structured with a sufficient amount of at least one polymer chosen from ethylenediamine/stearyl dimer tallate copolymer;
(ii) at least one amphiphilic compound chosen from amphiphilic compounds which are liquid at room temperature and have an HLB value of less than 12; and
(iii) at least one dyestuff,
wherein said composition is wax-free and non-migrating.

9. A structured cosmetic composition comprising:
(i) at least one continuous liquid fatty phase, wherein said at least one continuous liquid fatty phase is structured with a sufficient amount of at least one polymer chosen from ethylenediamine/stearyl dimer dilinoleate copolymer;
(ii) at least one amphiphilic compound chosen from amphiphilic compounds which are liquid at room temperature and have an HLB value of less than 12; and
(iii) at least one dyestuff,
wherein said structured composition is in the form of a non-migrating, wax-free solid, and
wherein said at least one continuous liquid fatty phase, said at least one polymer, said at least one amphiphilic compound, and said at least one dyestuff form a physiologically acceptable medium.

10. A process of structuring a cosmetic composition in the form of a physiologically acceptable composition, which is wax-free and non-migrating comprising including in said composition
(i) at least one liquid continuous fatty phase, said at least one liquid continuous fatty phase being structured with a sufficient amount of at least one polymer chosen from ethylenediamine/stearyl dimer dilinoleate copolymer;
(ii) at least one amphiphilic compound chosen from amphiphilic compounds which are liquid at room temperature and have an HLB value of less than 12; and
(iii) at least one dyestuff,
wherein said composition is wax-free and non-migrating.

* * * * *

UNITED STATES PATENT AND TRADEMARK OFFICE
CERTIFICATE OF CORRECTION

| | | |
|---|---|---|
| PATENT NO. | : 7,144,582 B1 | Page 1 of 1 |
| APPLICATION NO. | : 09/685577 | |
| DATED | : December 5, 2006 | |
| INVENTOR(S) | : Veronique Ferrari et al. | |

It is certified that error appears in the above-identified patent and that said Letters Patent is hereby corrected as shown below:

On the title page, item (57), line 7, "least continuous" should read --least one continuous--.

Signed and Sealed this

Sixth Day of March, 2007

JON W. DUDAS
*Director of the United States Patent and Trademark Office*